US012629184B2

(12) United States Patent
Zander

(10) Patent No.: US 12,629,184 B2
(45) Date of Patent: May 19, 2026

(54) DYNAMIC NAIL-PLATE COMBINATION

(71) Applicant: Stryker European Operations Limited, Carrigtwohill (IE)

(72) Inventor: Nils Zander, Eckernförde (DE)

(73) Assignee: Stryker European Operations Limited, Carrigtwohill (IE)

( * ) Notice: Subject to any disclaimer, the term of this patent is extended or adjusted under 35 U.S.C. 154(b) by 350 days.

(21) Appl. No.: 18/139,750

(22) Filed: Apr. 26, 2023

(65) Prior Publication Data

US 2024/0081881 A1 Mar. 14, 2024

Related U.S. Application Data

(60) Provisional application No. 63/334,946, filed on Apr. 26, 2022.

(51) Int. Cl.
*A61B 17/74* (2006.01)
*A61B 17/00* (2006.01)

(52) U.S. Cl.
CPC .......... *A61B 17/746* (2013.01); *A61B 17/744* (2013.01); *A61B 2017/00681* (2013.01); *A61B 2017/00982* (2013.01)

(58) Field of Classification Search
CPC ................ A61B 17/746; A61B 17/744; A61B 2017/00681; A61B 2017/00982; A61B 17/1717; A61B 17/7283; A61B 17/808; A61B 17/846; A61B 17/1721; A61B 17/1725; A61B 17/8061

USPC ...................................................... 606/62–68
See application file for complete search history.

(56) References Cited

U.S. PATENT DOCUMENTS

| | | | |
|---|---|---|---|
| 7,780,667 B2 | 8/2010 | Watanabe et al. | |
| 8,157,803 B1 * | 4/2012 | Zirkle, Jr. ............ | A61B 17/746 606/65 |
| 2007/0219636 A1 * | 9/2007 | Thakkar ............. | A61B 17/1721 623/18.11 |
| 2008/0004623 A1 * | 1/2008 | Ferrante ............... | A61B 17/746 606/62 |
| 2011/0190769 A1 * | 8/2011 | Haininger .......... | A61B 17/8061 606/64 |
| 2017/0265915 A1 * | 9/2017 | Langdale ........... | A61B 17/8057 |

* cited by examiner

*Primary Examiner* — Eduardo C Robert
*Assistant Examiner* — Tara Rose E Carter
(74) *Attorney, Agent, or Firm* — Lerner David LLP

(57) ABSTRACT

A fracture fixation system includes an intramedullary nail having a proximal nail hole, wherein an inner surface of the proximal nail hole has a non-circular shape in a plane perpendicular to an axis along which the proximal nail hole extends; a plate having an inner surface for placement against a surface of a bone, the plate defining a proximal plate hole adjacent a proximal end of the plate extending through the plate; and a peg extending along a peg axis and configured for insertion into the proximal nail hole, wherein a body of the peg has an outer surface defining a non-circular shape in a plane perpendicular to the peg axis, the peg further including a lateral end adjacent to the body and configured to engage the proximal plate hole, the lateral end having a reduced cross-section that is smaller than a maximum cross-section of the body of the peg.

20 Claims, 4 Drawing Sheets

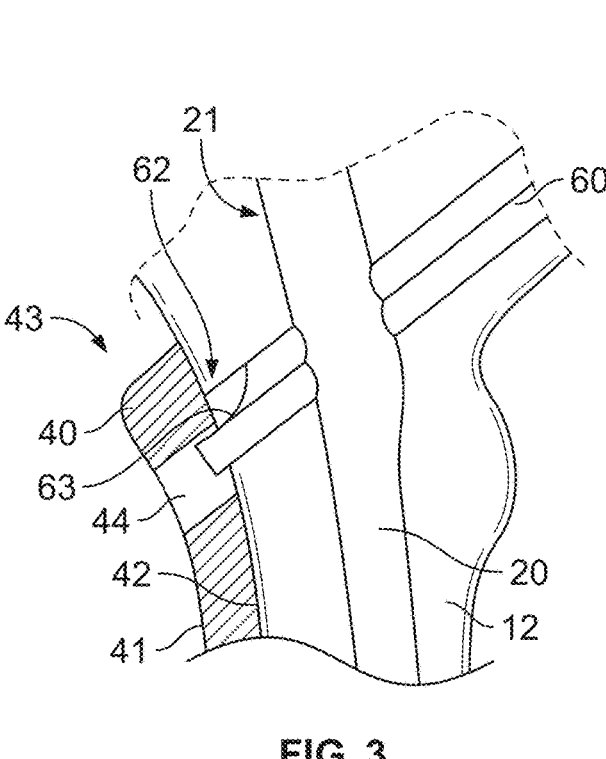
FIG. 3
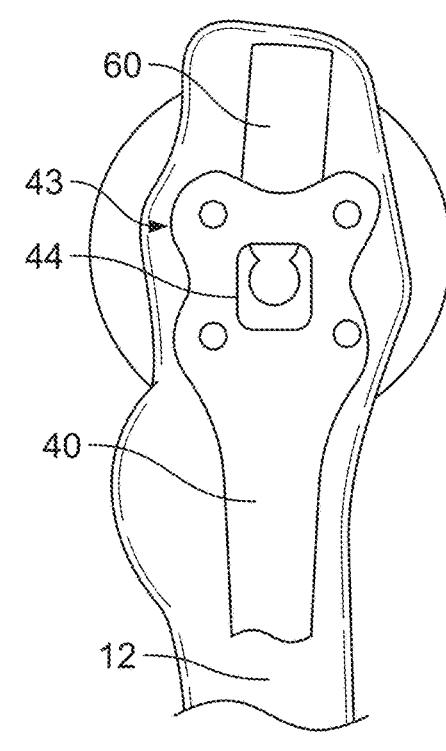
FIG. 4
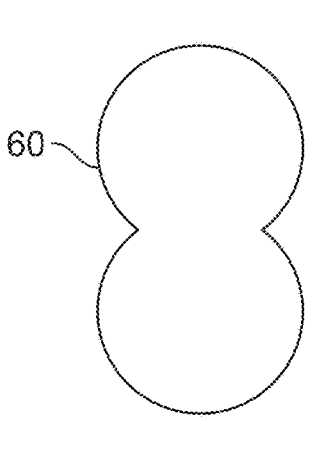
FIG. 5
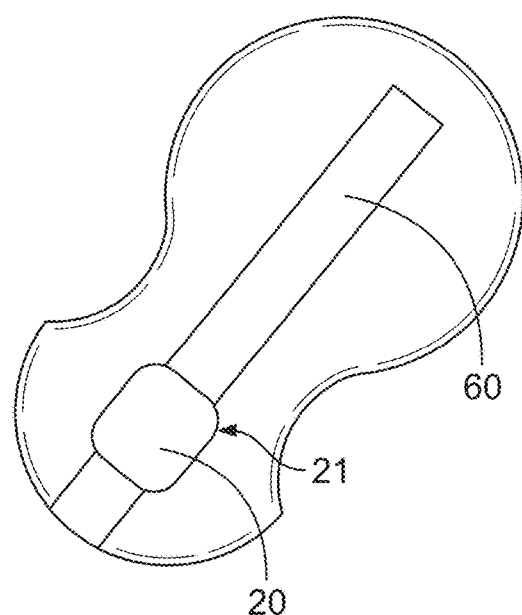
FIG. 6

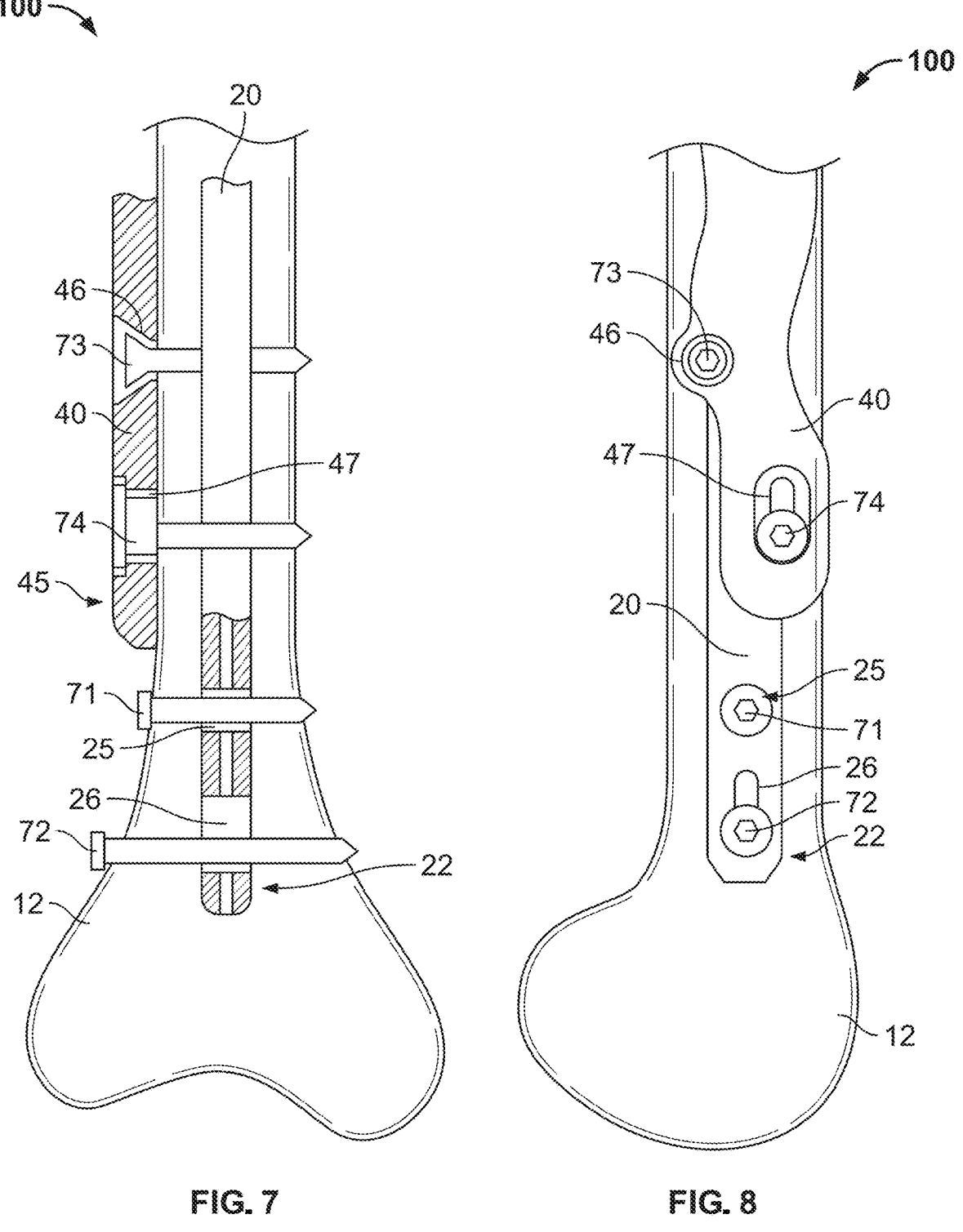
FIG. 7                    FIG. 8

DYNAMIC NAIL-PLATE COMBINATION

CROSS-REFERENCE TO RELATED APPLICATIONS

The present application claims the benefit of the filing date of U.S. Provisional Application No. 63/334,946, filed Apr. 26, 2022, the disclosure of which is hereby incorporated herein by reference.

BACKGROUND OF THE INVENTION

The surgical treatment of complex proximal femur fractures remains challenging and offers various options such as intramedullary nails and lateral plates, which are commonly used for the majority of both stable and unstable trochanteric fractures. However, the limitations of these devices are reached if fracture comminutions and/or the degree of instability raises a question as to the efficacy of the treatment options. This might be given in cases in which the proximal nail entry portal is not accessible or does not provide any means of implant support and/or comminution of the lateral wall would not allow a proper and mechanically sound placement of a lateral plate with sufficient *varus* prevention. Attempts to treat such kind of fractures with above mentioned methods often result in non-unions, *varus* malalignments and/or hardware failures, including secondary loss of fixation, which requires revision surgery.

Due to lack of alternatives, Lateral Proximal Femur Plates (LPFP) have been established as a potential option to treat these kinds of complex situations. Such plates are considered a last resort for an osteosynthesis with preservation of the patient's joint anatomy and function. Despite limited clinical utilization, LPFP appear an important component of a comprehensive plating portfolio to provide a solution for these rare but highly demanding clinical situations. Nevertheless, the above-mentioned systems are associated with insufficient biomechanical performance, high complication rates including hardware failures and revision rates and therefore they lack clinical acceptance. The reasons for increased level of construct failure are multi-factorial and the unfavorable biomechanics of a lateral plate construct in combination with complex fracture patterns and high bending moments appear obvious.

Accordingly, there is a need for new and improved fracture fixation systems that overcome these drawbacks.

BRIEF SUMMARY OF THE INVENTION

A first aspect of the present invention is a fracture fixation system, including an intramedullary nail having a proximal nail hole, wherein an inner surface of the proximal nail hole has a non-circular shape in a plane perpendicular to an axis along which the proximal nail hole extends, a lateral plate having an inner surface for placement against an exterior surface of a bone, the lateral plate defining a proximal plate hole at a proximal end of the lateral plate extending through the lateral plate, and a peg extending along a peg axis and configured for insertion into the proximal nail hole, wherein a body of the peg has an outer surface defining a non-circular shape in a plane perpendicular to the peg axis, the peg further including a lateral end adjacent to the body configured to engage the proximal plate hole, the lateral end having a reduced cross-section that is smaller than a maximum cross-section of the body of the peg.

In accordance with other embodiments of the first aspect, the non-circular shape of the outer surface of the peg and the non-circular shape of the proximal nail hole may match and permit lateral migration of the peg toward the lateral plate during healing of the fracture in the bone. The proximal plate hole may be elongated. The non-circular shape of the outer surface of the peg and the non-circular shape of the proximal nail hole may be figure-8 shapes.

The lateral plate may include additional plate holes at the proximal end for additional proximal fixation to the bone. The peg may be disposed through the proximal nail hole, the lateral end of the peg may be disposed within the proximal plate hole, and additional screws may extend respectively through additional plate holes of the lateral plate. The additional plate holes may not be aligned with any hole of the intramedullary nail, and the additional screws may not contact the intramedullary nail.

A proximal end of the intramedullary nail may have a cross-section that is larger than a cross-section of a remainder of the intramedullary nail located distally of the proximal end. In the intramedullary nail, the proximal nail hole may be at a proximal end thereof, and the intramedullary nail may further include a distal circular nail hole and a distal elongated nail hole at a distal end thereof, and the lateral plate may further include a distal circular plate hole and a distal elongated plate hole at a distal end thereof.

A first screw may be disposed in the circular nail hole at the distal end of the intramedullary nail, a second screw may be disposed in the distal elongated nail hole at the distal end of the intramedullary nail, a third screw may be disposed in the distal circular plate hole at the distal end of the lateral plate and does not contact the intramedullary nail, and a fourth screw may be disposed in the distal elongated plate hole at the distal end of the lateral plate and does not contact the intramedullary nail. The lateral plate may define a central axis extending from the proximal end to the distal end, the distal circular plate hole and the distal elongated plate hole may both be offset within the lateral plate so that neither intersects the central axis. The distal circular plate hole and the distal elongated plate hole may be offset on different sides of the central axis.

A second aspect of the present invention is a fracture fixation system, including an intramedullary nail having a distal circular nail hole and a distal elongated nail hole at a distal end, a lateral plate having an inner surface for placement against an exterior surface of a bone, the lateral plate defining a distal circular plate hole and a distal elongated plate hole at a distal end of the lateral plate each extending through the lateral plate, and a first screw is disposed in the distal circular nail hole at the distal end of the intramedullary nail, a second screw is disposed in the distal elongated nail hole at the distal end of the intramedullary nail, a third screw is disposed in the distal circular plate hole at the distal end of the lateral plate and does not contact the intramedullary nail, and a fourth screw is disposed in the distal elongated plate hole at the distal end of the lateral plate and does not contact the intramedullary nail.

In accordance with other embodiments of the second aspect, the lateral plate may define a central axis extending from the proximal end to the distal end, the distal circular plate hole and the distal elongated plate hole may both be offset within the lateral plate so that neither intersects the central axis. The distal circular plate hole and the distal elongated plate hole may be offset on different sides of the central axis.

A third aspect of the present invention is a method of fixing a bone fracture, including inserting an intramedullary nail into a canal of a long bone, the intramedullary nail having a distal circular nail hole and a distal elongated nail hole at a distal end thereof, placing an inner surface of a lateral plate against an exterior surface of a bone, the lateral plate defining a distal circular plate hole and a distal elongated plate hole at a distal end of the lateral plate each extending through the lateral plate, inserting a first screw into the distal circular nail hole at the distal end of the intramedullary nail, inserting a second screw into the distal elongated nail hole at the distal end of the intramedullary nail, inserting a third screw into the distal circular plate hole at the distal end of the lateral plate and avoiding contact with the intramedullary nail, and inserting a fourth screw into the distal elongated plate hole at the distal end of the lateral plate and avoiding contact with the intramedullary nail.

In accordance with other embodiments of the third aspect, the intramedullary nail may have a proximal nail hole at a proximal end thereof, an inner surface of the proximal nail hole having a non-circular shape in a plane perpendicular to an axis along which the proximal nail hole extends, the lateral plate may define a proximal plate hole at a proximal end thereof, and the method may further include a step of inserting a peg into the proximal nail hole, the peg extending along a peg axis, wherein a body of the peg has an outer surface defining a non-circular shape in a plane perpendicular to the peg axis, the peg further including a lateral end adjacent to the body configured to engage the proximal plate hole, the lateral end having a reduced cross-section that is smaller than a maximum cross section of the body of the peg. The non-circular shape of the outer surface of the peg and the non-circular shape of the proximal nail hole may permit lateral migration of the peg toward the lateral plate during healing of the fracture in the bone.

The step of inserting the intramedullary nail may include using a targeting arm attached to the proximal end of the intramedullary nail. The targeting arm may include an interface for mating with the lateral plate, and the step of installing the lateral plate may occur after the step of inserting the intramedullary nail and includes engaging the lateral plate to a positioner of the targeting arm to align the lateral plate with respect to the intramedullary nail. The targeting arm may include screw guides to align with additional plate holes at the proximal end of the lateral plate, and the method may further include installing fixation screws into the additional plate holes, respectively, and into the proximal portion of the bone, wherein none of the fixation screws contacts the intramedullary nail.

The method may further include removing the first screw from the circular nail hole at the distal end of the intramedullary nail, and/or removing the third screw from the distal circular plate hole at the distal end of the lateral plate. The method may further include drilling a superior bore through the femoral neck and into the femoral head, and drilling an inferior bore through the femoral neck and into the femoral head to at least partially overlap the superior bore to create a bore hole having a figure-8 shape. The steps of drilling may include drilling through a double-barreled drill sleeve to remove the bone. The method may further include inserting a k-wire through a femoral neck and into a femoral head before the steps of drilling the first and second bores. The step of drilling the superior bore may include drilling the superior bore over the k-wire.

An assembled configuration of the system includes the peg disposed through the proximal nail hole, the lateral plate secured to the bone, and the reduced cross-section of the lateral end of the peg disposed within the proximal plate hole.

BRIEF DESCRIPTION OF THE DRAWINGS

The drawings described herein are for illustrative purposes only of the selected embodiments and are not all possible implementations and thus are not intended to limit the scope of the present disclosure.

FIG. 3 is a sectional view of the intersection of the nail, the plate, and the peg of the system shown in FIG. 1.

FIG. 4 is a side view of the system shown in FIG. 1.

FIG. 5 is a cross sectional view of the peg of the system shown in FIG. 1.

FIG. 6 is a top view of the nail and the peg of the system shown in FIG. 1.

FIGS. 7 and 8 are perspective views of a distal end of the system shown in FIG. 1.

DETAILED DESCRIPTION

Figures 1, 2:
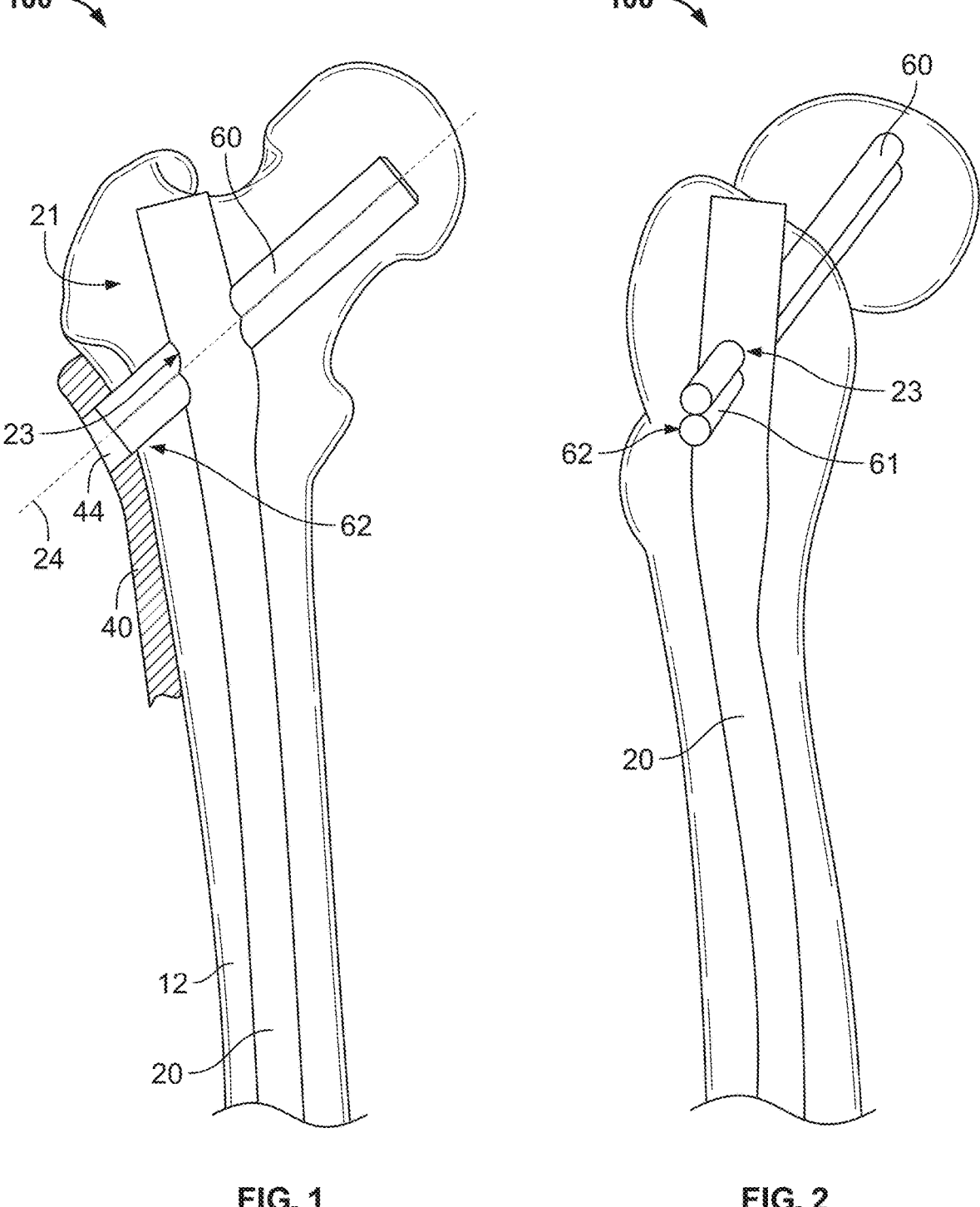
FIGS. 1 and 2 are perspective views of a proximal end of a fracture fixation system of the present invention implanted in a femur.

For this invention, dedicated attention has been drawn to the attempt to maintain dynamic locking principles for both sub-implant systems involved if required for unrestricted fixation healing. The clinical failures of the prior art mentioned in the background section above are often seen in cases of delayed/non-unions of the sub-trochanteric region which could be associated with the static locking principle of the implants used.

Clinical monitoring of fracture healing progression includes the option for secondary dynamization in cases of delayed or impending non-unions. In such situations, surgeons remove static locking screws from the construct within a (limited) surgical interventions thus altering the mechanical environment in favor for improved fracture healing. An approach switching the locking mode from static to an axially dynamic situation is provided herein for both implant types utilized, i.e. the plate and the nail.

The biomechanical advantage of intramedullary rods for fracture fixation in long bones is well described with literature. Beside the favorable biomechanics in proximal femur situations (reduced lever arm to accept resulting hip forces), especially the underlying dynamic principle in various directions (e.g. sliding of cephalic component and option for distal dynamic locking via an oblong hole) is believed to be highly useful for good clinical performance even in difficult situations.

As used herein, the term "proximal," when used in connection with a device or components of a device, refers to the end of the device closer to the user of the device (e.g., surgeon or operator) when the device is being used as intended. On the other hand, the term "distal," when used in connection with a device or components of a device, refers to the end of the device farther away from the user (e.g., surgeon or operator) when the device is being used as intended. As used herein, the term "superior" refers to an upward direction on the page or relative to an anatomy of a person standing upright. On the other hand, the term "inferior" refers to a downward direction on the page or relative to an anatomy of a person standing upright. It should be understood that these terms are not limiting, but merely used for ease of description, and that varied orientations may cause directions to differ. As used herein, the terms "substantially," "generally," "approximately" and "about" are intended to mean that slight deviations from absolute are included within the scope of the term so modified.

A first embodiment of a fracture fixation system 100 is shown in FIGS. 1-9 and includes an intramedullary nail 20, a lateral plate 40, and a peg 60. System 100 is designed for use in a femur 12, although use of all or some of the components of system 100 in other bones, such as the tibia or humerus for example, is also contemplated for assistance in fracture fixation.

Nail 20 is designed for use in an intramedullary canal of a long bone, and extends longitudinally along an axis from a proximal end 21 to a distal end 22. At proximal end 21, a non-circular proximal nail hole 23 is provided for use with peg 60. The non-circular configuration is provided by an inner surface of proximal nail hole 23 having a non-circular shape, which is referenced in a plane perpendicular to an axis 24 along which proximal nail hole 23 extends, as shown in FIG. 1. Axis 24 is a central axis of proximal nail hole 23, which is unthreaded and is non-circular in order to prevent rotation of peg 60 when it is disposed therein due to the similar or matching cross-sections, as explained further below.

As shown in FIGS. 7 and 8, at distal end 22 of nail 20, a circular distal nail hole 25 and an elongated distal nail hole 26 are provided for fixing nail 20 in the bone. Either or both of holes 25 and 26 can be threaded. While described as circular and designed for closely securing an inserted a screw, distal nail hole 25 may be other shapes that are not exactly circular, such as funnel or slightly elongated, or may be enlarged and circular. Ultimately, distal nail hole 25 is designed to hold a screw in a static configuration with respect to nail 20. On the other hand, elongated distal nail hole 26 is designed so that the position of a screw within elongated distal nail hole 26 can move relative to nail 20 as healing progresses.

Proximal end 21 of nail 20 has an enlarged cross-section that is larger compared to the rest of nail 20. Additional locking screws provided in plate 40 can pass into the neck of femur 12 in a more direct line without connecting with nail 20. In other words, assembly of system 100 provides for interconnection between nail 20 and plate 40, while additional fixation can take place between femur 12 and nail 20, and/or femur 12 and plate 40. Adjacent proximal end 21 of nail 20, the enlarged proximal end 21 provides a sturdy end of nail 20 for connection to tools and easy insertion, while the relatively slimmer profile of nail 20 just distal and adjacent to the enlarged proximal end 21 permits the additional locking screws to pass closer to the midline or central axis of nail 20 to remain embedded in the bone on a trajectory toward a central portion of the head of femur 12. This design of nail 20 is also shown in FIG. 6, where proximal end 21 is designed to be narrower in the anterior-posterior direction than it is in the medial-lateral direction when implanted, such that it has an oval, oblong, or obround shape. In some cases, the relatively thinner width of nail 20, i.e. in the anterior-posterior direction, could be the same as the width of nail 20 distally of the proximal end 21, such that the enlargement is pronounced only in the medial-lateral direction. The nonrotational asymmetric cross-section of proximal end 21 of nail 20 provides for stabilization within femur 12 and cooperation with other components of system 100.

Plate 40 has an outer surface 41 and an inner surface 42 for placement against an exterior surface of femur 12. In a proximal end 43 of plate 40, a proximal plate hole 44 extends through plate 40 for reception of a lateral end of peg 60, as described further below. Proximal plate hole 44 is elongated, preferably with an oval, oblong, or obround shape. As shown in FIGS. 7 and 8, at a distal end 45 of plate 40, a circular distal plate hole 46 and an elongated distal plate hole 47 are included to extend through plate 40 from outer surface 41 to inner surface 42 for securing plate 40 to femur 12. As with the holes described above in connection with distal end 22 of nail 20, either or both of holes 46 and 47 can be threaded, and distal plate hole 46 may be other shapes that are not exactly circular, such as funnel or slightly elongated, or may be enlarged and circular. Plate 40 can include additional plate holes 48 at proximal end 43 for the additional locking screws, which can be variable angle locking screws, to provide additional proximal fixation to femur 12 anterior and posterior of the implanted nail 20 to appropriately secure proximal fragments when needed. Plate holes 48 are preferably not aligned with any holes of nail 20 when system 100 is in its assembled configuration, i.e. with proximal plate hole 44 aligned with proximal nail hole 23. That is, the central axis of any of plate holes 48 is not coaxial with the central axis of any of the holes in nail 20. In this way, the additional locking screws can be inserted directly and only into femur 12 to avoid nail 20 so that that the additional locking screws can be dedicated to securing plate 40 to femur 12 and do not contact nail 20.

As shown in FIGS. 7 and 8, circular distal plate hole 46 and elongated distal plate hole 47 are both offset from a midline or central axis of plate 40. Holes 46 and 47 can be offset on the same or different sides from the midline. The axis or midline of plate 40 can be defined at a location proximal of holes 46 and 47, such that distal end 45 of plate 40 is wavy or otherwise provides sections that deviate from the extension of the midline. In this way, neither of holes 46 and 47 are aligned with nail 40 so that screws inserted in holes 46 and 47 do not intersect or contact nail 40 at all, allowing such screws to focus solely on securing plate 40 to femur 12. In other words, neither of holes 46, 47 intersects or overlaps the extension of the midline or central axis of plate 40.

Peg 60 is a cephalic component of system 100 shown in FIGS. 1-3 to extend along a peg axis that coincides with axis 24 of proximal nail hole 23 when peg 60 is inserted therein. A body of peg 60 has an outer surface 61 that defines a non-circular shape similar to that of proximal nail hole 23 so that a mating engagement can be achieved. The non-circular shape is also defined within a plane perpendicular to the peg axis. The non-circular shape of the outer surface of peg 60 and the non-circular shape of proximal nail hole 23, which can be figure-8 shapes, match or have equivalently shaped perimeters in order to permit lateral migration of peg 60 toward plate 40 during healing of the fracture in femur 12. Other non-circular shapes can also be used, such as rectangular, triangular, star-shaped, or any other geometry that inhibits rotation of peg 60 about its axis when peg 60 is disposed within proximal nail hole 23. In this way, the implanted peg 60 resists hip forces and inhibits or reduces the risk of rotation of the femoral head fragment during healing. The non-circular design also allows for a reduced dimension in the anterior-posterior direction, thus limiting the required dimensioning of nail 20.

At a lateral end 62 of peg 60, an upper ramped or stepped edge 63 is provided to engage with or be located within proximal plate hole 44. In this regard, the elongated shape of proximal plate hole 44 provides space to ease simultaneous positioning of the components of system 100 by allowing a certain amount of distal migration of nail 20, and therefore peg 60 mated with nail 20, relative to plate 40. Proximal plate hole 44 can be of the smallest possible dimension while maintaining contact between peg 60 and the inferior cortex and still allowing a dynamic principle of the peg 60. Edge 63 is most clearly shown in FIG. 3, where an inferior surface of peg 60 is linear and aligned with the peg axis all the way to the terminal end of peg 60, while a superior surface of peg is linear until it meets edge 63, and the profile at lateral end 62 then reduces until the terminal end of peg 60. In lateral end 62, a cross-section of peg 60 is smaller than a cross-section of the remainder of the body of peg 60. While ramped edge 63 is not shown as clearly in FIGS. 1 and 2, edge 63 can be provided in those depictions as well.

With a distal end of peg 60 embedded in the neck and/or head of femur 12, the nonthreaded and geometrically mating engagement of peg 60 with proximal nail hole 23 of nail 20 makes it possible for peg to migrate laterally toward plate 40. This allows lateral support for peg 60 distally while having the smallest possible opening of proximal plate hole 44 to increase the strength of plate 40. The relatively small size of proximal plate hole 44 is made possible by the relatively smaller cross-section of lateral end 62 of peg 60.

System 100 is constructed for dynamic movement at both its proximal and distal ends. In the proximal end, dynamic lateral sliding of peg 60 is possible, as described above. In the distal end, the use of elongated distal nail hole 26 and elongated distal plate hole 47 permit additional dynamic distal/inferior movement of nail 20 and plate 40 after implantation, which is explained further below in connection with the method of using system 100.

Figure 9:
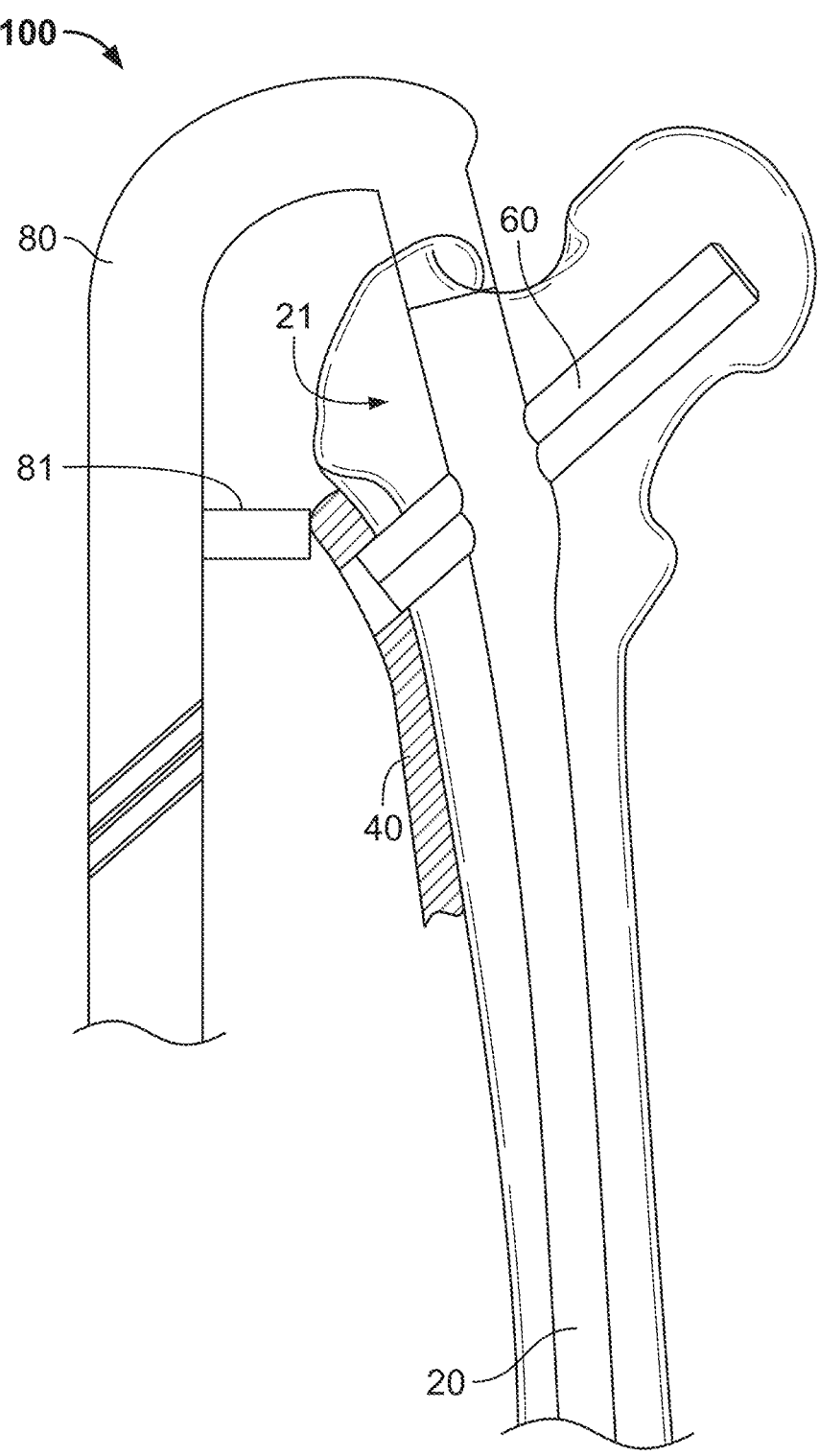
FIG. 9 is a perspective view of an insertion step of the system shown in FIG. 1 using a targeting arm.

A method of using system 100 includes inserting nail 20 into a canal of femur 12, and placing inner surface 42 of plate 40 against an exterior surface of femur 12. This can be done using a targeting arm 80 attached to proximal end 21 of nail 20, with targeting arm 80 including an extended plate positioner 81 as an interface to provide a reference point or a physical stop or guide at which to abut or mate with plate 40 so that it is aligned properly with nail 20 as shown in FIG. 9. Digital fluoroscopy can also be used to assist in placement of nail 20 and/or plate 40 and to verify the relative positions of all components of system 100. Positions of nail 20 and plate 40 can be corrected if necessary. Targeting arm 80 also includes plate locking screw guides 82 to align with additional plate holes at proximal end 43 of plate 40. This facilitates an additional step in which screws 48 are installed into holes and into femur 12 without such screws being inserted into nail 20. Thus, nail 20 is inserted into femur 12 and targeting arm 80 provides a specific location at which plate 40 is set against the bone, so that any plate locking screws are certain to be inserted through the plate 40 to lock it into the bone while missing and not contacting nail 20. In some embodiments, other screw guides in targeting arm 80 can be provided to guide screws or fasteners into plate 40 and also into nail 20 to facilitate linking of the structures. Alternative to the use of targeting arm 80, a targeting block attached to the plate surface might be used. As noted above, none of screws 48 is inserted to contact nail 20. While it is described that no contact occurs, it is of course possible that screws 48 can rest upon an outer surface of nail 20 but would not impede the movement of nail 20 during healing. This is also the case for screws provided at the distal end of the system that mate with plate 40 but not nail 20.

A first screw 71 is inserted into circular distal nail hole 25 and a second screw 72 is inserted into elongated distal nail hole 26. A third screw 73 is inserted into circular distal plate hole 46 and a fourth screw 74 is inserted into elongated distal plate hole 47. While screws 71 and 72 are of course inserted into communication with nail 20, screws 73 and 74 are purposely inserted in a manner that avoids contact with nail 20. In this way, plate 40 is anchored to femur 12 at distal end 45 in a manner that is isolated from nail 20. As shown in FIGS. 7 and 8, this includes placement of screws 73 and 74 so that one is on each side of nail 20.

The method further includes inserting peg 60 into proximal nail hole 23. This can be done before insertion of plate 40, which permits proximal plate hole 44 to be smaller in cross section than the full body cross section (distal of lateral end 62). In other embodiments in which proximal plate hole 44 may be of a larger cross section than the maximum cross-section of peg 60, peg 60 can be inserted after installation of plate 40. To prepare for insertion of peg, a k-wire can be inserted through the neck and into the head of femur 12. Superior and inferior bores can be drilled through the neck and into the head of femur 12. One of the bores can be drilled over the k-wire if present. The bores can at least partially overlap to create a bore hole having a figure-8 shape to accept peg 60. This can include drilling through a double-barreled drill sleeve to remove the bone. Of course if peg 60 takes on another non-circular form, the hole for peg 60 can be drilled according to such geometry. Peg 60 can be inserted into femur 12 without further distal fixation, or in other embodiments a screw can be inserted within a cannulation of peg 60 to anchor peg 60 within the head of femur 12.

If it is determined by a surgeon that additional dynamic movement of nail 20 with respect to plate 40 would be beneficial or would further facilitate healing and/or bone growth, for optional secondary dynamization in cases of delayed or impending sub-trochanteric non-unions a revision step can remove static screws 71 and 73 in a limited surgical intervention to alter the mechanical environment in favor of improved fracture healing. This effectively switches the locking mode from static to an axially dynamic, and ensures rotational control while allowing axial dynamization of the fracture. That is, screws 71 and 73 are static screws since circular distal nail hole 25 and circular distal plate hole 46 do not allow for any movement between the respective screws 71, 73 and nail 20 or plate 40 during healing, i.e. in a direction along the axis of femur 12. However, screws 72 and 74 placed in elongated distal nail hole 26 and elongated distal plate hole 47 are effectively dynamically placed screws since the elongated nature of holes 26 and 47 allow movement between the respective screws 72, 74 and nail 20 and plate 40 during healing in a direction along the axis of femur 12. Thus, a revision step can include removing screw 71 and/or screw 73 to facilitate healing by movement of nail 20 and/or plate 40, respectively, with respect to femur 12.

In cases where only proximal plate locking is desired, a shorter plate relative to the length of nail 20 can be utilized. In the same regard, a separate distal plate could be used to facilitate the distal static and dynamic locking as described herein.

In other variations of system 100, nail 20 and plate 40 can be included without peg 60. In this way, only the distal dynamization of system 100 would be utilized based on static and dynamic screw insertion and selective removal of the static screws. More or fewer holes in nail 20 and/or plate 40 can be included according to need. Still in other variations of system 100, peg 60 can be included with nail 20 and plate 40, but only static screws 71 and 73 may be utilized to focus system 100 only on proximal dynamization.

Each component of system 100, including all of the screws, can be made of any surgical grade rigid material such as plastic, ceramic, or metal, and particularly various metals such as titanium, titanium alloys, stainless steel, cobalt chrome alloys, tantalum and niobium, or any combination thereof. Gold and/or silver can be provided in the material composition or as a coating of a component, and any other similar metal-ion releasing element or material can be provided as an antimicrobial substance.

Each component of system 100, including all of the screws, may be formed by an additive manufacturing process, including but not limited to electron beam melting (EBM), selective laser sintering (SLS), selective laser melting (SLM), binder jet printing, and blown powder fusion for use with metal powders. Any of the components can be manufactured by 3D printing.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fracture fixation system, comprising:
an intramedullary nail having a proximal nail hole, wherein an inner surface of the proximal nail hole has a non-circular shape in a plane perpendicular to an axis along which the proximal nail hole extends;
a plate having an inner surface for placement against an exterior surface of a bone, the plate defining a proximal plate hole adjacent a proximal end of the plate extending through the plate; and
a peg extending along a peg axis and configured for insertion into the proximal nail hole, wherein a body of the peg has an outer surface defining a non-circular shape in a plane perpendicular to the peg axis, the peg further including a lateral end adjacent to the body and configured to engage the proximal plate hole, the lateral end having a reduced cross-section that is smaller than a maximum cross-section of the body of the peg,
wherein the peg is disposed through the proximal nail hole and the lateral end of the peg is disposed within the proximal plate hole.

2. The fracture fixation system of claim 1, wherein the non-circular shape of the outer surface of the body of the peg and the non-circular shape of the inner surface of the proximal nail hole match.

3. The fracture fixation system of claim 2, wherein the proximal plate hole is elongated.

4. The fracture fixation system of claim 2, wherein the non-circular shape of the outer surface of the body of the peg and the non-circular shape of the inner surface of the proximal nail hole are figure-8 shapes.

5. The fracture fixation system of claim 1, wherein the plate includes additional plate holes at the proximal end for additional proximal fixation to the bone, and additional screws extend respectively through the additional plate holes of the plate, wherein respective central axes of the additional plate holes are not coaxial with a central axis of any hole of the intramedullary nail, and the additional screws do not contact the intramedullary nail.

6. The fracture fixation system of claim 1,
wherein in the intramedullary nail, the proximal nail hole is at a proximal end thereof, and the intramedullary nail further comprises a distal circular nail hole and a distal elongated nail hole at a distal end thereof, and
wherein the plate further comprises a distal circular plate hole and a distal elongated plate hole at a distal end thereof.

7. The fracture fixation system of claim 6, wherein:
a first screw is disposed in the distal circular nail hole;
a second screw is disposed in the distal elongated nail hole;

a third screw is disposed in the distal circular plate hole and does not contact the intramedullary nail; and
a fourth screw is disposed in the distal elongated plate hole and does not contact the intramedullary nail.

8. The fracture fixation system of claim 6, wherein the plate defines a central axis extending from the proximal end to the distal end, the distal circular plate hole and the distal elongated plate hole are both offset within the plate so that neither intersects the central axis.

9. The fracture fixation system of claim 8, wherein the distal circular plate hole and the distal elongated plate hole are offset on different sides of the central axis.

10. A method of fixing a bone fracture, comprising:
inserting an intramedullary nail into a canal of a long bone, the intramedullary nail having a distal circular nail hole and a distal elongated nail hole at a distal end thereof;
placing an inner surface of a plate against an exterior surface of a bone, the plate defining a distal circular plate hole and a distal elongated plate hole at a distal end of the plate each extending through the plate;
inserting a first screw into the distal circular nail hole;
inserting a second screw into the distal elongated nail hole;
inserting a third screw into the distal circular plate hole and avoiding contact with the intramedullary nail; and
inserting a fourth screw into the distal elongated plate hole and avoiding contact with the intramedullary nail.

11. The method of claim 10, wherein:
the intramedullary nail has a proximal nail hole at a proximal end thereof, an inner surface of the proximal nail hole having a non-circular shape in a plane perpendicular to an axis along which the proximal nail hole extends;
the plate defines a proximal plate hole at a proximal end thereof; and
the method further comprises a step of inserting a peg into the proximal nail hole, the peg extending along a peg axis, wherein a body of the peg has an outer surface defining a non-circular shape in a plane perpendicular to the peg axis, the peg further including a lateral end adjacent to the body configured to engage the proximal plate hole, the lateral end having a reduced cross-section that is smaller than a maximum cross section of the body of the peg.

12. The method of claim 11, wherein the non-circular shape of the outer surface of the peg and the non-circular shape of the proximal nail hole permit lateral migration of the peg toward the plate during healing of the fracture in the bone.

13. The method of claim 11, further comprising:
drilling a superior bore through a femoral neck and into a femoral head; and
drilling an inferior bore through the femoral neck and into the femoral head to at least partially overlap the superior bore to create a bore hole having a figure-8 shape.

14. The method of claim 13, wherein the steps of drilling include drilling through a double-barreled drill sleeve to remove the bone.

15. The method of claim 13, further comprising inserting a k-wire through the femoral neck and into the femoral head before the steps of drilling the superior and inferior bores.

16. The method of claim 15, wherein the step of drilling the superior bore includes drilling the superior bore over the k-wire.

17. The method of claim 10, wherein the step of inserting the intramedullary nail includes using a targeting arm attached to the proximal end of the intramedullary nail, the targeting arm includes an interface for mating with the plate, and the step of installing the plate occurs after the step of inserting the intramedullary nail and includes engaging the plate to a positioner of the targeting arm to align the plate with respect to the intramedullary nail.

18. The method of claim 10, wherein the step of inserting the intramedullary nail includes using a targeting arm attached to the proximal end of the intramedullary nail, the targeting arm includes screw guides to align with additional plate holes at the proximal end of the plate, and further comprising installing fixation screws into the additional plate holes, respectively, and into the proximal portion of the bone, wherein none of the fixation screws contacts the intramedullary nail.

19. The method of claim 10, further comprising removing the first screw from the circular nail hole at the distal end of the intramedullary nail, and/or removing the third screw from the distal circular plate hole at the distal end of the plate.

20. A method of fixing a bone fracture, comprising:

inserting an intramedullary nail into a canal of a long bone, the intramedullary nail having a proximal nail hole, an inner surface of the proximal nail hole having a non-circular shape in a plane perpendicular to an axis along which the proximal nail hole extends;

inserting a peg into the proximal nail hole, the peg extending along a peg axis, wherein a body of the peg has an outer surface defining a non-circular shape in a plane perpendicular to the peg axis; and placing an inner surface of a plate against an exterior surface of a bone, the plate defining a proximal plate hole, wherein the peg further includes a lateral end adjacent to the body disposed within the proximal plate hole, the lateral end having a reduced cross-section that is smaller than a maximum cross section of the body of the peg.

* * * * *